United States Patent
Lehmann et al.

(10) Patent No.: US 7,151,252 B2
(45) Date of Patent: Dec. 19, 2006

(54) RADIATION PHANTOM WITH HUMANOID SHAPE AND ADJUSTABLE THICKNESS

(75) Inventors: Joerg Lehmann, Pleasanton, CA (US); Joshua Levy, Salem, NY (US); Robin L. Stern, Lodi, CA (US); Christine Hartmann Siantar, Livermore, CA (US); Zelanna Goldberg, Carmichael, CA (US)

(73) Assignee: The Regents of the University of California, Oakland, CA (US)

(*) Notice: Subject to any disclaimer, the term of this patent is extended or adjusted under 35 U.S.C. 154(b) by 233 days.

(21) Appl. No.: 10/915,889

(22) Filed: Aug. 11, 2004

(65) Prior Publication Data

US 2005/0035282 A1    Feb. 17, 2005

Related U.S. Application Data

(60) Provisional application No. 60/495,446, filed on Aug. 14, 2003.

(51) Int. Cl.
*G01D 18/00* (2006.01)

(52) U.S. Cl. .................................................. 250/252.1
(58) Field of Classification Search .............. 250/252.1
See application file for complete search history.

(56) References Cited

U.S. PATENT DOCUMENTS

| | | | |
|---|---|---|---|
| 3,010,223 A * | 11/1961 | Alderson | 434/267 |
| 5,164,978 A | 11/1992 | Goodenough et al. | |
| 5,165,050 A | 11/1992 | Goodenough et al. | |
| 5,227,627 A * | 7/1993 | Gamarnik et al. | 250/252.1 |
| 5,506,884 A | 4/1996 | Goodenough et al. | |
| 6,362,471 B1 | 3/2002 | Spitz et al. | |
| 6,668,073 B1 | 12/2003 | Robar et al. | |
| 2004/0017936 A1 | 1/2004 | Gopinath et al. | |

* cited by examiner

*Primary Examiner*—David Porta
*Assistant Examiner*—Mindy Vu
(74) *Attorney, Agent, or Firm*—Eddie E. Scott

(57) ABSTRACT

A radiation phantom comprising a body with a general humanoid shape and at least a portion having an adjustable thickness. In one embodiment, the portion with an adjustable thickness comprises at least one tissue-equivalent slice.

5 Claims, 2 Drawing Sheets

RADIATION PHANTOM WITH HUMANOID SHAPE AND ADJUSTABLE THICKNESS

CROSS-REFERENCE TO RELATED APPLICATIONS

This application claims benefit of U.S. Provisional Patents Application No. 60/495,446, filed Aug. 14, 2003 and titled "Radiation Patent with Humanoid Shape and Adjustable Thickness." U.S. Provisional Patent Application No. 60/495,446 filed Aug. 14, 2003 and titled "Radiation Phantom with Humanoid Shape and Adjustable Thickness" is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to radiation phantoms and more particularly to a radiation phantom with humanoid shape and adjustable thickness.

2. State of Technology

U.S. Pat. No. 5,506,884 to David J. Goodenough and Joshua R. Levy for a radiation phantom and test methods employing the same issued Apr. 9, 1996 provides the following state of technology information, "X-ray phantoms are known calibration devices and teaching aids for conventional x-ray machines. Prior art phantoms are available in a number of variations, some being plastic replicas of the human body or specific portions thereof, while others consist of actual human bones cast in plastic. These phantoms are used to train x-ray technicians in the proper positioning of the human body for the various x-ray images that are taken for diagnosis, and the resulting films may be studied to aid in calibrating an x-ray machine for identifying the radiographic image of known structures."

U.S. Pat. No. 6,668,073 to James L. Robar and Brenda G. Clark for an anthropomorphic film phantom for three-dimensional dosimetry issued Dec. 23, 2003 provides the following state of technology information, "Stereotactic radiosurgery is a method for treating brain lesions, using collimated convergent beams of x-ray photons produced by a clinical linear accelerator. In order to conform the administered dose distribution to the delineated volume of the lesion, while sparing healthy adjacent tissue, the method requires an extremely high spatial accuracy of approximately ±1 millimeter (mm). The method also requires an accuracy of ±2% in controlling the magnitude of the administered dose. Because the success of stereotactic radiosurgery hinges on the accurate delivery of dosage of x-ray photons to the lesion, simulated radiosurgery using a suitable phantom, or a pseudo-object, is performed prior to actual application of the radiosurgery to a human patient, to record and verify the resulting dose distribution. The result of the simulated radiosurgery may be used to adjust stereotactic radiosurgery parameters to ensure that the desired dose distribution is applied to a human patient."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a radiation phantom comprising a body with a general a humanoid shape and at least a portion of said body having an adjustable thickness. In clinical radiation therapy, many patients do not correspond to the standard body shapes and sizes, being either overweight or, in some cases, cachextic as a consequence of their cancer. Scattering conditions and therefore accurate dosimetry depends upon the precise amount of patient tissue located along the path length of the particles. Therefore, if the point of interest is located outside of the field, the patient's thickness is a critical factor in accurate dose determination. In the radiation phantom of the present invention at least a portion of said body has an adjustable thickness. In one embodiment, the portion with an adjustable thickness comprises at least one tissue-equivalent slice.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 2:
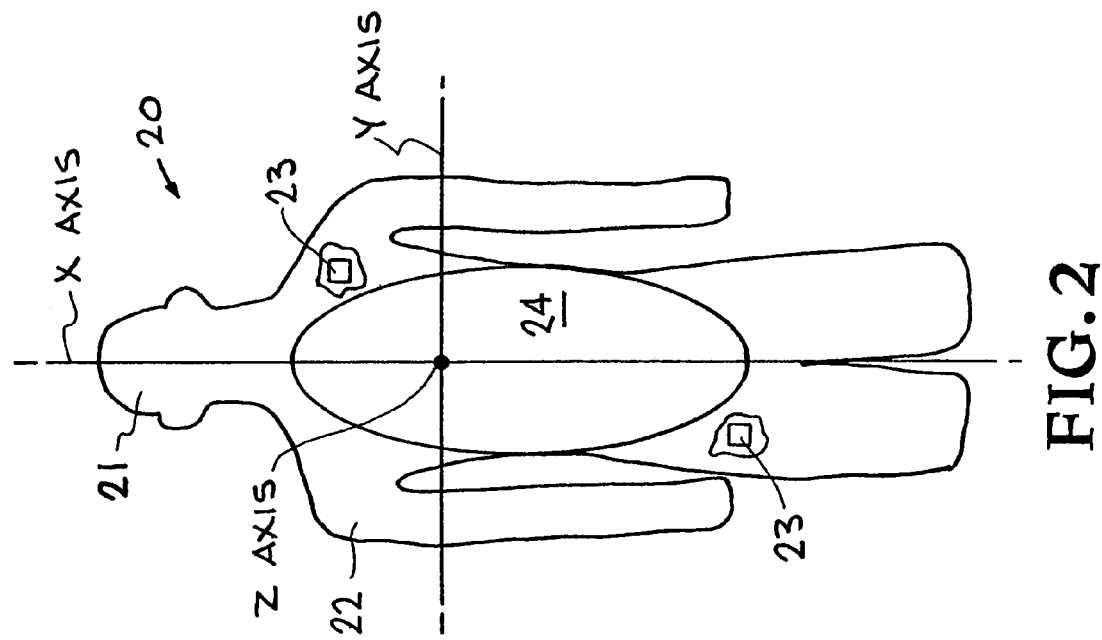
FIG. 2 an embodiment of a radiation phantom constructed in accordance with the present invention is illustrated.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Figure 1:
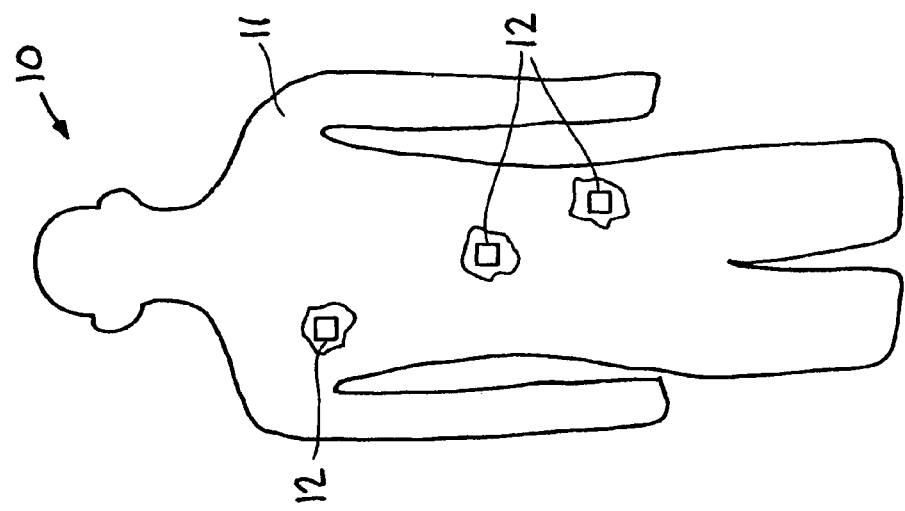
FIG. 1 a radiation phantom is illustrated.

Referring now to FIG. 1, a radiation phantom is illustrated. The radiation phantom is designated generally by the reference numeral 10. The radiation phantom 10 can be constructed with a natural human skeleton cast 11 inside material that is radiologically equivalent to soft tissue. Two models of the radiation phantom 10 correspond to the "standard man" and the "standard woman." The radiation phantom 10 includes radiation detectors 12. For example, the radiation detectors can be dosimeters.

Referring now to FIG. 2, a radiation phantom constructed in accordance with the present invention is illustrated. The radiation phantom is designated generally by the reference numeral 20. The radiation phantom has a head 21 and body 22. An X axis is shown extending vertically through the center of the radiation phantom 20. A Y axis is shown extending horizontally through the center of the radiation phantom 20 perpendicular to the Y axis. A Z axis is shown extending into and out of the paper through the center of the radiation phantom 20 perpendicular to the Y axis and the Y axis.

In clinical radiation therapy, many patients do not correspond to the standard body shapes and sizes, being either overweight or, in some cases, cachextic as a consequence of their cancer. Scattering conditions and therefore accurate dosimetry depends upon the precise amount of patient tissue located along the path length of the particles. Therefore, if the point of interest is located outside of the field, the patient's thickness is a critical factor in accurate dose determination.

The radiation phantom 20 includes radiation detectors 23. For example, the radiation detectors can be dosimeters. The radiation phantom 20 has a humanoid shape with at least a portion 24 having an adjustable thickness through the insertion or removal of a variable number of tissue-equivalent slices. The portion 24 and the tissue-equivalent slices extend along the Z axis.

Figure 3:
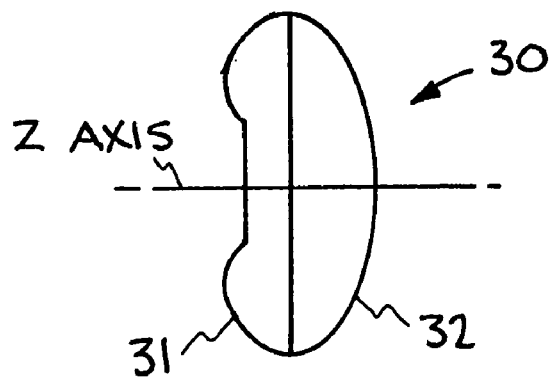
FIG. 3 illustrates an embodiment of a radiation phantom with a humanoid shape and an adjustable thickness.
Figure 4:
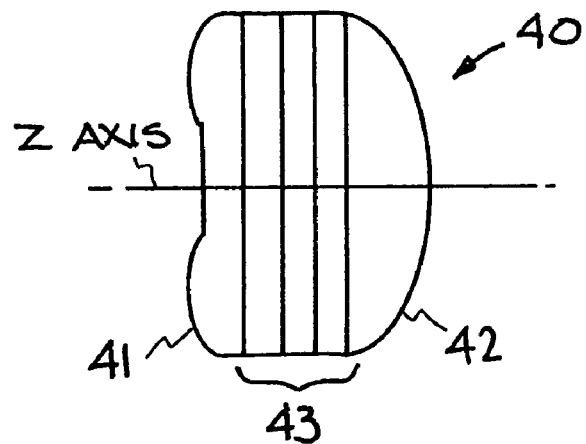
FIG. 4 illustrates an embodiment of a radiation phantom with a humanoid shape and an adjustable thickness.
Figure 5:
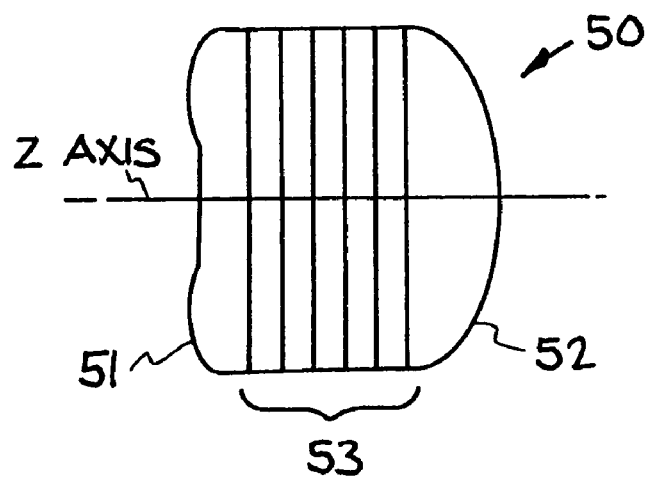
FIG. 5 illustrates an embodiment of a radiation phantom with a humanoid shape and an adjustable thickness.

Referring now to FIGS. 3, 4, and 5, embodiments of a radiation phantom with a humanoid shape and an adjustable thickness constructed in accordance with the present invention are shown. The radiation phantom embodiments are designated generally by the reference numerals 30, 40, and 50.

The humanoid shape body radiation phantom 30 is illustrated in FIG. 3. The humanoid shape body radiation phantom 30 has a tissue-equivalent posterior section 31 and a tissue-equivalent anterior section 32. The tissue-equivalent posterior section 31 and the tissue-equivalent anterior section 32 are shown positioned along the Z axis. For reference, the Z axis corresponding to the Z axis shown in FIG. 2. As will be explained subsequently, tissue equivalent slices can be added to provide the humanoid shape body radiation phantom 30 with an adjustable thickness.

Referring now to FIG. 4, the humanoid shape body radiation phantom 40 is illustrated. The humanoid shape body radiation phantom 40 has a tissue-equivalent posterior section 41 and a tissue-equivalent anterior section 42. The tissue-equivalent posterior section 41 and the tissue-equivalent anterior section 42 are located along the Z axis. Three tissue-equivalent slices identified by the reference numeral 43 are added between the tissue-equivalent posterior section 41 and the tissue-equivalent anterior section 42. The tissue-equivalent slices 43 extend along the Z axis. A variable thickness is provided by adding one, two, or three of the tissue-equivalent slices 43 between the tissue-equivalent posterior section 41 and the tissue-equivalent anterior section 42.

Referring now to FIG. 5, the humanoid shape body radiation phantom 50 is illustrated. The humanoid shape body radiation phantom 50 has a tissue-equivalent posterior section 51 and a tissue-equivalent anterior section 52. The tissue-equivalent posterior section 51 and the tissue-equivalent anterior section 42 are located along the Z axis. Five tissue-equivalent slices identified by the reference numeral 53 are added between the tissue-equivalent posterior section 51 and the tissue-equivalent anterior section 52. The tissue-equivalent slices 53 extend along the Z axis. A variable thickness is provided by adding one, two, three, four, or five of the tissue-equivalent slices 53 between the tissue-equivalent posterior section 51 and the tissue-equivalent anterior section 52.

The radiation phantoms 30, 40, and 50 with Humanoid shape and Adjustable Thickness (RPHAT) is a tissue-equivalent anthropomorphic phantom sliced in the coronal direction, which is designed for radiation oncology clinical and research use. The tissue-equivalent posterior sections, the tissue-equivalent anterior sections, and the central slices are shaped to allow a variable number of central slices to be inserted while maintaining the anthropomorphic shape.

Applicants have built and tested a prototype. The prototype is designated a Phantom with Humanoid shape and Adjustable Thickness (RPHAT). It provides a robust new model for radiation studies.

In the prototype, RPHAT, there are five central slices each of which is 2.5–2.7 cm thick. Therefore, anthropomorphic phantoms ranging in total thickness from 18.1 cm to 30.7 cm can be generated from this single-base structure. RPHAT was designed to investigate the capability of a Monte Carlo system to simulate dose delivery in a multi-beam treatment outside of any of the primary beams. The goal of the study was to identify areas of the abdominal skin of a prostate radiotherapy patient that received 1 and 10 cGy in a single fraction (prescription dose 2 Gy).

Since the desired dose was equivalent to between 0.5% and 5% of the prescribed dose the location of such dose on the skin was outside the radiation area. No primary beam reached the points of interest in the given situation, and therefore all of the dose measured is due to scatter. Thus, the amount of scattering material is crucial and a 'standard man' phantom would not have generated sufficiently accurate scattering conditions to mirror the actual clinical scenario under study.

For the clinical study, a Monte Carlo algorithm was used to find the locations of the low dose. With RPHAT Applicants analyzed the accuracy of the Monte Carlo system in the 'real-world' multi-beam situation.

Thermoluminescence detectors (TLD) were used on the surface of the phantom under a layer of bolus, accurately modeling the patient set-up. Applicants found a consistent under prediction of the dose by the Monte Carlo algorithm (15–20%), which was phantom-thickness dependent at the size extremes. RPHAT allowed the determination of the relationship between the scatter dose outside the beam and the patient thickness. Such an investigation would not have been possible with previous phantoms.

Phantoms constructed in accordance with the present invention provide a valuable addition to the tool chest of medical physicists, which allows quality assurance measurements for a variety of patient thicknesses. For research purposes, phantoms constructed in accordance with the present invention facilitate the investigation of the influence of patient thickness as an independent dosimetry parameter. Outside of the primary beam scatter dose from within the patient is the main source of radiation to the peripheral tissues. Although single-beam measurements can be obtained using a slab-shaped phantom, for multiple-beam treatment it is desirable to use an anthropomorphically shaped phantom to properly model the true scatter pathways. Intrapatient scatter is an important area of research as it represents a significant portion of the dose delivered from an Intensity Modulated Radiation Therapy (IMRT) plan, as well as being a critical component in other radiation-related research.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A radiation phantom, comprising:
    a body with a general a humanoid shape including a body with a center; said body having an X axis extending vertically through said body and said center, a Y axis extending horizontally through said body and said center, and a Z axis extending perpendicular to said X axis and said Y axis and extending through said center; and
    an open portion in said body located along said Z axis and extending through said center; said open portion in said body receiving a removable tissue equivalent unit having an adjustable thickness, said removable tissue equivalent unit removable along said Z axis.

2. The radiation phantom of claim 1, wherein said removable tissue equivalent unit having an adjustable thickness comprises a tissue equivalent posterior section, a tissue equivalent anterior section, and at least one tissue-equivalent slice located between said tissue equivalent posterior section and said tissue equivalent anterior section, said at least one tissue-equivalent slice being planar.

3. The radiation phantom of claim 1, wherein said removable tissue equivalent section having an adjustable thickness comprises a tissue equivalent posterior section, a tissue equivalent anterior section, and a multiplicity of tissue-equivalent slices located between said tissue equivalent posterior section and said tissue equivalent anterior section, each said tissue-equivalent slice being planar.

4. The radiation phantom of claim 1, wherein said at least one tissue-equivalent slice comprises a flat slice with a central axis extending along said Z axis.

5. The radiation phantom of claim 1, wherein said multiplicity of tissue-equivalent slices are substantially identical in size shape extending along said Z axis.

* * * * *